(12) United States Patent
Straub

(10) Patent No.: US 8,568,432 B2
(45) Date of Patent: Oct. 29, 2013

(54) CATHETER FOR ASPIRATING, FRAGMENTING AND REMOVING EXTRACTABLE MATERIAL FROM BLOOD VESSELS

(75) Inventor: Immanuel Straub, Wangs (CH)

(73) Assignee: Straub Medical AG., Wangs (CH)

( * ) Notice: Subject to any disclaimer, the term of this patent is extended or adjusted under 35 U.S.C. 154(b) by 107 days.

(21) Appl. No.: 13/129,951

(22) PCT Filed: Nov. 5, 2009

(86) PCT No.: PCT/IB2009/054909
§ 371 (c)(1),
(2), (4) Date: Jun. 21, 2011

(87) PCT Pub. No.: WO2010/061308
PCT Pub. Date: Jun. 3, 2010

(65) Prior Publication Data
US 2011/0313346 A1    Dec. 22, 2011

(30) Foreign Application Priority Data

Nov. 27, 2008   (CH) ...................................... 1850/08

(51) Int. Cl.
*A61B 17/22*   (2006.01)

(52) U.S. Cl.
USPC ........................................................ 606/159

(58) Field of Classification Search
USPC .................. 606/159, 167, 170, 177–180, 79; 604/19, 22
See application file for complete search history.

(56) References Cited

U.S. PATENT DOCUMENTS

| 2,026,630 | A | 1/1936 | Harris |
| 3,082,805 | A | 3/1963 | Royce |

(Continued)

FOREIGN PATENT DOCUMENTS

| DE | 10162933 A1 | 7/2003 |
| EP | 0310285 A2 | 4/1989 |

(Continued)

OTHER PUBLICATIONS

International Search Report for corresponding PCT Application PCT/IB2009/054909, dated Apr. 3, 2010.

(Continued)

*Primary Examiner* — Elizabeth Houston
(74) *Attorney, Agent, or Firm* — Matthew B. Dernier, Esq.; Gibson & Dernier LLP

(57) ABSTRACT

The invention relates to a catheter for aspirating, fragmenting and removing extractable material from hollow bodies, in particular thrombi and emboli from blood vessels, with a working head, which is arranged at the distal end of the catheter, is axially displaceable along a guide wire, independently thereof, and comprises at least one lateral opening. The catheter comprises a flexible feed screw which has a distal end and a proximal end and which can be rotated at a speed of rotation by means of a rotary drive of a drive unit remote from the working head. A flexible tube which surrounds the feed screw and is connected to the working head removes the material or the detached thrombi and emboli fragments. The feed screw is designed as a shearing cutting tool which cooperates with the opening in the working head in order to size-reduce and remove the materials or aspirated and/or detached thrombi and emboli which penetrate between the peripheral edges of the feed screw and edges of the openings. A thrust bearing is arranged between the distal end of the feed screw and the working head so as to axially support the feed screw, and is designed as a disc which can be rotated by the feed screw during operation.

15 Claims, 3 Drawing Sheets

(56) References Cited

U.S. PATENT DOCUMENTS

| | | |
|---|---|---|
| 3,732,858 A | 5/1973 | Banko |
| 3,945,375 A | 3/1976 | Banko |
| 4,705,511 A | 11/1987 | Kocak |
| 4,844,064 A | 7/1989 | Thimsen et al. |
| 4,857,046 A | 8/1989 | Stevens et al. |
| 4,867,157 A | 9/1989 | McGurk-Burleson et al. |
| 4,935,025 A | 6/1990 | Bundy et al. |
| 5,078,723 A | 1/1992 | Dance et al. |
| 5,084,052 A | 1/1992 | Jacobs |
| 5,100,426 A | 3/1992 | Nixon |
| 5,226,909 A | 7/1993 | Evans et al. |
| 5,312,425 A | 5/1994 | Evans et al. |
| 5,417,703 A | 5/1995 | Brown et al. |
| 5,569,178 A | 10/1996 | Henley |
| 5,571,122 A | 11/1996 | Kelly et al. |
| 5,833,704 A | 11/1998 | McCombs |
| 5,873,882 A | 2/1999 | Straub et al. |
| 6,217,565 B1 | 4/2001 | Cohen |
| 6,565,588 B1 | 5/2003 | Clement et al. |
| 7,905,896 B2 | 3/2011 | Straub |
| 2002/0010487 A1 | 1/2002 | Evans |
| 2003/0114875 A1 | 6/2003 | Sjostrom |
| 2007/0219484 A1 | 9/2007 | Straub |

FOREIGN PATENT DOCUMENTS

| | | |
|---|---|---|
| EP | 0448859 A2 | 10/1991 |
| EP | 0448859 A3 | 5/1992 |
| EP | 0267539 B1 | 4/1993 |
| EP | 0582533 A1 | 2/1994 |
| EP | 0669106 A2 | 8/1995 |
| EP | 0680730 A2 | 11/1995 |
| EP | 0680730 A3 | 1/1996 |
| EP | 0739603 A1 | 10/1996 |
| EP | 0669106 B1 | 2/1999 |
| EP | 0739603 B1 | 8/2001 |
| JP | H05-78207 U | 10/1993 |
| JP | H10-277047 A | 10/1998 |
| JP | H11-506358 A | 6/1999 |
| JP | 2002-538876 A | 11/2002 |
| JP | 2005-512631 A | 5/2005 |
| WO | 91/01114 A | 2/1991 |
| WO | 94/24941 A1 | 11/1994 |
| WO | 96/29941 A1 | 10/1996 |
| WO | 00/47116 A1 | 8/2000 |
| WO | 00/54659 A1 | 9/2000 |
| WO | 02/49690 A2 | 6/2002 |
| WO | 02/49690 A3 | 6/2002 |
| WO | 2005/084562 A2 | 9/2005 |
| WO | 2005/084562 A3 | 9/2005 |

OTHER PUBLICATIONS

International Preliminary Report on Patentability and Written Opinion for corresponding PCT Application PCT/IB2009/054909, dated May 31, 2011.

English translation of the IPRP and Written Opinion of the International Search Authority for for corresponding PCT/IB2009/054909, dated Jun. 9, 2011.

File history of copending U.S. Appl. No. 13/030,165, filed Feb. 18, 2011, based on WO 2005/84562 cited as document D1 in the PCT-ISR search of the present application.

International Search report for corresponding PCT/IB2009/054909, dated Mar. 4, 2010.

English translation of the IPRP and Written Opinion of the International Search Authority for copending PCT/IB2005/000543, dated Sep. 11, 2007.

Statement of Relevancy for Japanese applications cited above, Dec. 2, 2010.

CATHETER FOR ASPIRATING, FRAGMENTING AND REMOVING EXTRACTABLE MATERIAL FROM BLOOD VESSELS

BACKGROUND

The invention relates to a catheter for aspirating, fragmenting and removing extractable material from hollow bodies, in particular thrombi and emboli from blood vessels, with a working head, which is arranged at the distal end of the catheter, is axially displaceable along a guide wire, independently thereof, and comprises at least one lateral opening, the catheter comprising a flexible feed screw which has a distal part and a proximal part and which can be rotated at a speed of rotation by means of a rotary drive of a drive unit remote from the working head, and with a flexible tube which surrounds the feed screw and is connected to the working head to remove the material or the detached thrombi and emboli fragments, and with a cutting tool, the feed screw being designed as a shearing cutting tool which cooperates with the opening in the working head in order to size-reduce the materials or aspirated and/or detached thrombi and emboli which penetrate between the peripheral edges of the feed screw and edges of the openings.

WO 2005/084562 A2, in the name of the applicant, discloses catheters which are used in particular to remove fresh blood clots from blood vessels in order to prevent these clots from blocking narrow regions and obstructing the blood vessels ('embolisms'). The content of WO 2005/084562 A2, in particular in terms of the embodiments disclosed therein of openings in the working head of the catheter, is hereby included in full scope as a component of the present application (FIGS. 6-10: rectangular lateral opening; FIGS. 11-15, claim 10: working head with a narrow slit extending in the longitudinal direction of the working head; FIGS. 16-20: approximately square lateral opening; FIGS. 21-25, claim 11: slitted opening extending in the peripheral direction of the working head; FIGS. 26-30, claims 15-17: grooved recess proceeding from the distal end of the working head and opening out into the lateral opening; FIGS. 31-35: working head with a lateral opening formed as an elongate slit and a grooved recess proceeding from the distal end of the working head and opening out into the lateral opening; FIGS. 36-40: approximately triangular lateral opening, of which the width narrows towards the proximal end; FIGS. 41-60 and claims 3, 4 and 14: lateral opening which consists of a region extending in the axial direction and a region extending over a part of the periphery of the working head, again having different embodiments of the partial regions of the opening in accordance with the description of the figures on page 11; FIGS. 61-65: opening extending along a screw line of the feed screw; FIGS. 66-80: opening extending along a screw line of the feed screw and which opens out into a region of the opening extending in the axial direction).

WO 96/29941 A1 discloses a rotary catheter for atherectomy, of which the working head consists of a stationary stator connected to a tube and a rotor. The rotor is rotatable relative to the stator by means of a high-speed feed/drive screw. Both the stator and the rotor have apertures over their periphery which can be aligned. The parts protruding or aspirated into the openings are size-reduced by shearing between a blade on the rotor and a counter-blade on the openings in the stator. The rotor can surround the stator externally ('external rotor') or may be arranged inside the rotor (Internal rotor'). This rotary catheter is used, above all, where relatively hard and rather brittle coatings have formed over time on the inner wall of blood vessels, such as veins and the like. However, the design according to WO 2005/084562 A2 is better adapted for the removal of fresh blood clots (such as thrombi) from blood vessels.

The content of WO 96/29941 A1, in particular in terms of the embodiments disclosed therein of openings in the stator and rotor, is hereby also included in full scope as a component of the present application (FIGS. 2, 3, 6, 7, 9, 10 and 12 with substantially oval through-openings in the stator and in the rotor, in conjunction with the corresponding parts of the description: p. 5, lines 23-24 and p. 8, lines 14-33 with reference to FIG. 2; p. 5, line 26 and p. 9, lines 1-17 with reference to FIG. 3; p. 6, lines 2-4 and p. 10, lines 24-28 with reference to FIG. 6; p. 6, lines 6-7 and p. 10, line 30 to p. 11, line 3 with reference to FIG. 7; p. 6, lines 12-14 and pages 15-16 with reference to FIG. 9; p. 6, lines 16-18 and p. 11, lines 15-16 with reference to FIG. 10; p. 6, lines 23-24 and p. 11, line 18 to p. 12, line 28 with reference to FIG. 12).

The blood clots to be removed are often very fibrous and tough and can only be removed in part with effort and at high cost in terms of time and equipment, or else cannot be removed at all. Sometimes the obstructing material blocks the threads of the feed screw, so hardly any more material can be conveyed. If the feed screw becomes blocked then it may become damaged and the catheter thus becomes useless.

U.S. Pat. No. 5,569,178 A discloses a catheter in which the distal end of the feed screw is mounted in a thrust bearing which is provided in a corresponding recess.

SUMMARY OF THE INVENTION

The object of the invention is therefore to provide a catheter which makes it possible to remove thrombi and emboli in a rapid, uninterrupted and complete manner, even under difficult conditions.

In accordance with the invention this is achieved in that a thrust bearing is arranged between the distal end of the feed screw and the working head, and is designed as a disc which can be rotated by the feed screw during operation.

Such a thrust bearing takes up the axial stresses which are generated on the feed screw in particular when material is conveyed from the distal end of the catheter to the proximal end of the catheter. This solution is simple and specific in terms of construction. The outer diameter of the disc corresponds approximately to the outer diameter of the feed screw, and the inner diameter of the disc corresponds approximately to the outer diameter of the guide wire.

When driving the feed screw a relative rotation occurs between the feed screw and the disc, as a result of which said disc is extended distally by axial pressure. In order to prevent any frictional heat, which damages the blood, the disc advantageously consists of a material with a low coefficient of friction, preferably of plastics material. A relatively hard material should be selected in order to avoid abrasion where possible.

The feed screw can expediently be biased under axial pressure. The axial biasing forces are taken up by the thrust bearing. The feed screw is thus arranged in a defined state from the start of operation. Vibrations can be largely reduced or prevented.

Depending on the type of obstructing material and the position of the points of the blood vessel which are to be opened, the requirements of the catheter may differ. The biasing pressure of the feed screw is thus advantageously adjustable. The biasing force is preferably adjusted ex-factory.

The biasing pressure of the feed screw is expediently set in such a way that the thrust bearing co-rotates approximately at half the speed of rotation of the feed screw. A relative difference in rotational speed is thus produced between the thrust bearing and the working head on the one hand, and between the thrust bearing and the feed screw on the other, this difference measuring approximately half of the speed of rotation of the feed spiral. The development of heat can thus be reduced and abrasion of the components which move relative to one another can thus be minimised or eliminated.

In order to prevent the openings in the working head from becoming blocked by the obstructing material to be removed, it is advantageous for the at least one lateral opening in the working head to be designed as a circular hole with a circumference. The circular shape of the hole provides a cross-section which is favourable in relation to size and is also favourable in terms of flow.

An expedient solution consists in the at least one lateral opening in the working head being formed as at least two holes which are arranged axially in succession. The cross-section of the opening can be directly multiplied by a plurality of holes.

With the arrangement of a plurality of holes arranged axially in succession, the circumferences of the holes advantageously overlap. The individual holes thus together form a common opening with a plurality of different cutting edges.

The holes may also expediently be interconnected by a slit extending in the axial direction and arranged substantially centrally to the holes, either instead of the overlapping arrangement of the holes or else in addition to such an arrangement. Such a slit not only increases the cross-section of the opening, but also forms additional blades for size reduction of the material to be removed.

The rear, drive-side region of the openings poses a particular risk with regard to the obstructing material to be removed becoming stuck between the feed screw and the lateral openings in the working head. It is therefore advantageous for the slit to extend beyond the holes toward the proximal end of the catheter. Additional cutting edges arranged in the axial direction are thus formed in this at-risk region.

Two approximately diametrically opposed openings are expediently formed on the working head. As a result of two diametrically opposed openings not only is the cross-section increased, but the number of cutting edges and therefore the number of cutting procedures per revolution of the catheter is also doubled.

In order to enable effective cutting procedure for the size reduction of the material to be removed in the catheter, the outer diameter of the distal part of the feed screw in the region of the working head is advantageously designed so as to fit precisely against the inner diameter of the preferably cylindrical working head, in such a way that the outer diameter of the feed screw has only minimal diametrical play relative to the inner diameter of the inner surface of the working head. Parts of the material to be removed are thus prevented from infiltrating the gap between the feed screw and the working head and from becoming stuck on either side between the working head and the feed screw.

The material to be removed which has been aspirated into the catheter is subjected to cutting and shearing procedures as a result of the cooperation between the rotating feed screw and the openings in the working head. In order for these cutting procedures to be carried out in an optimal manner, the edges on the outer face of the feed screw are expediently sharp-edged in the region of the opening in the working head. This makes it possible to shear off the, generally very tough, thrombi and emboli which are to be removed in an effective and clean manner.

The working head is expediently tapered toward its distal end. It is thus possible for the catheter to be slidingly inserted, even into narrow radii of curvature of the blood vessels, without a great amount of resistance. In addition, it also cannot hook onto the wall of the vessel or onto protrusions of the blood vessels.

The edges of the lateral openings are advantageously sharp-edged, at least over portions, on the inner face. Together with the periphery of the feed screw, it is thus possible to carry out a clean shearing procedure in order to fragment the thrombi or emboli. The openings in the working head are constructed in such a way that the feed screw, which rotates at high speed, fragments aspirated thrombi and emboli into small particles at the inner sharp edges of the openings and at the periphery of the feed screw. These particles, which are suspended in the blood, are fed toward the rotary drive by the prevailing vacuum and the action of the feed screw.

The edges of the lateral opening are expediently rounded, at least over portions, on the outer surface of the working head. This makes it possible for the deposits which are to be removed and for other aspirated bodily fluids (for example blood) to flow in a practically irrotational manner in the region of the working head.

Further embodiments of the invention are given in the drawings and in the dependent claims.

The list of reference numerals is a component of the disclosure.

The invention will now be described in greater detail symbolically and by way of example with reference to the drawings.

BRIEF DESCRIPTION OF THE DRAWINGS

The drawings will be described coherently and comprehensively. Like reference numerals denote like components; reference numerals with different indices denote functionally like or similar components.

In the drawings.

DETAILED DESCRIPTION OF THE INVENTION

Figure 1:
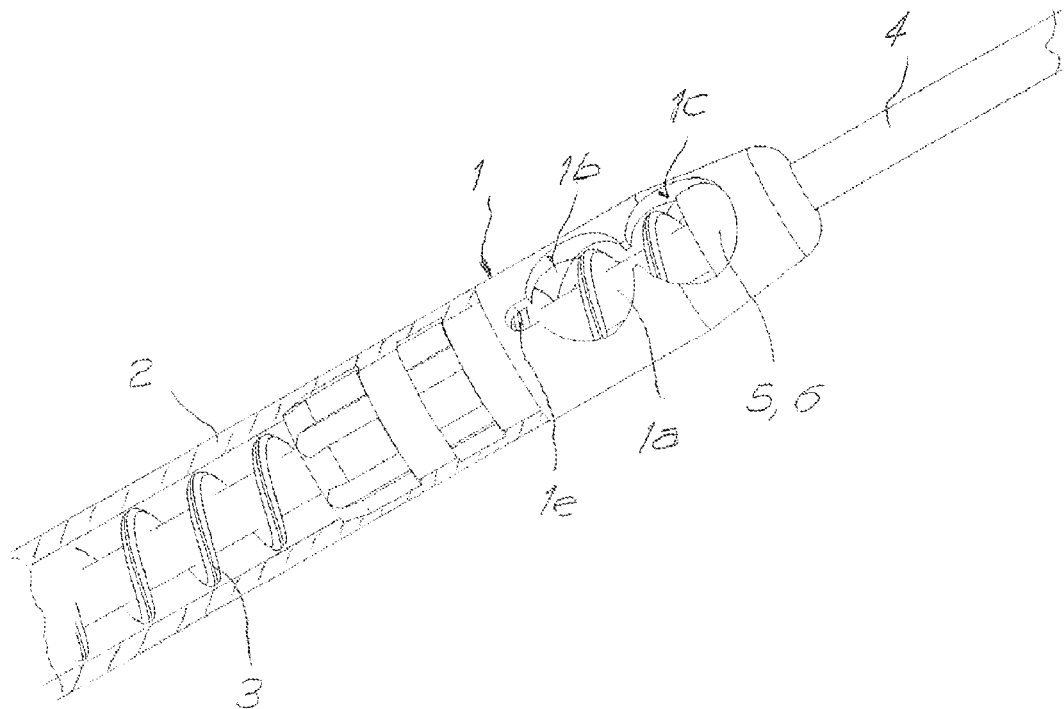
FIG. 1 is a perspective view of a catheter according to the invention.
Figure 2:
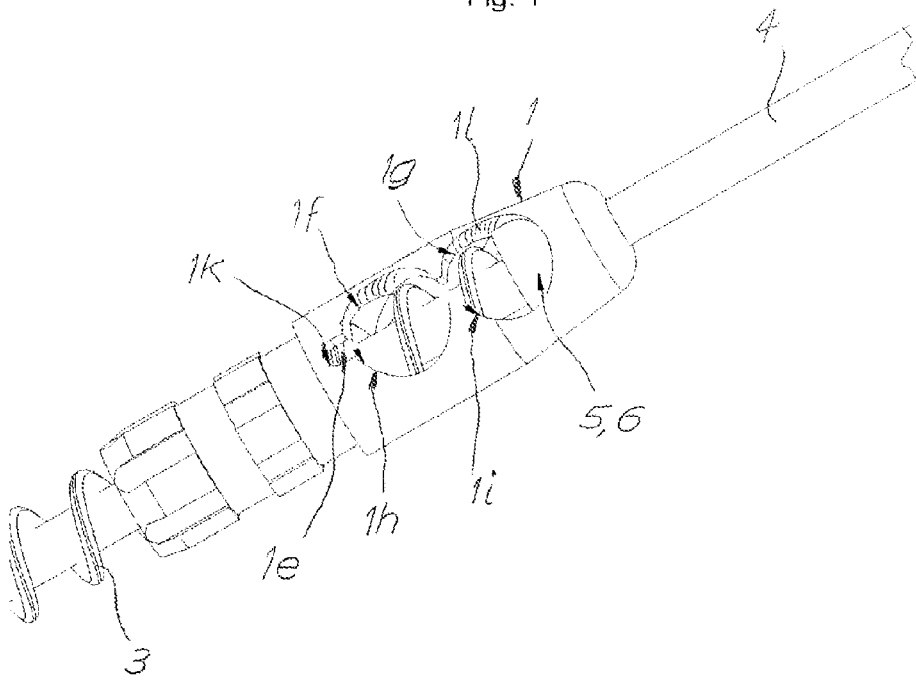
FIG. 2 shows the end region of the catheter according to FIG. 1.
Figure 3:
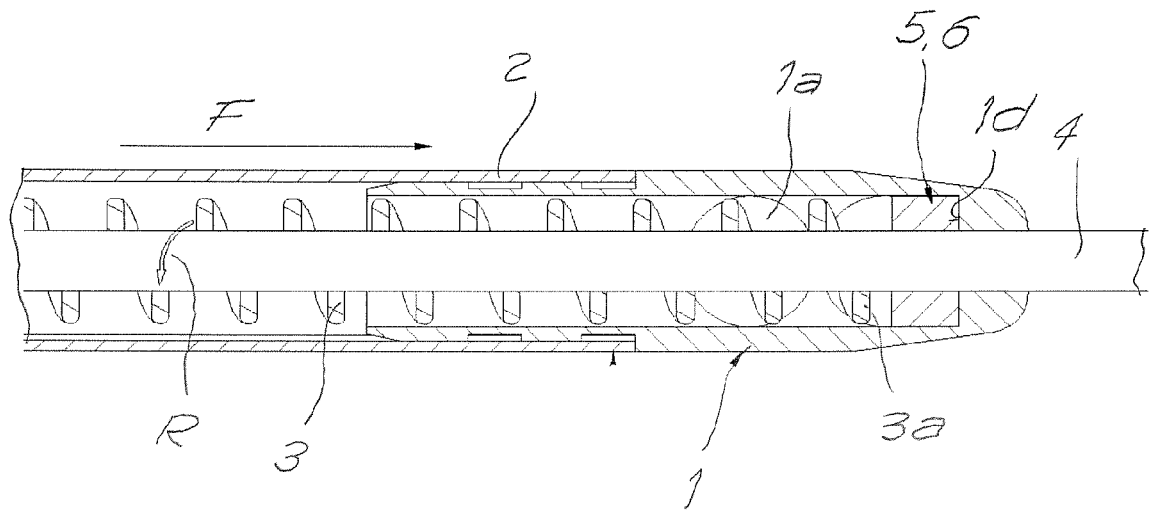
FIG. 3 is a longitudinal section of the catheter according to FIGS. 1 and 2.
Figure 4:
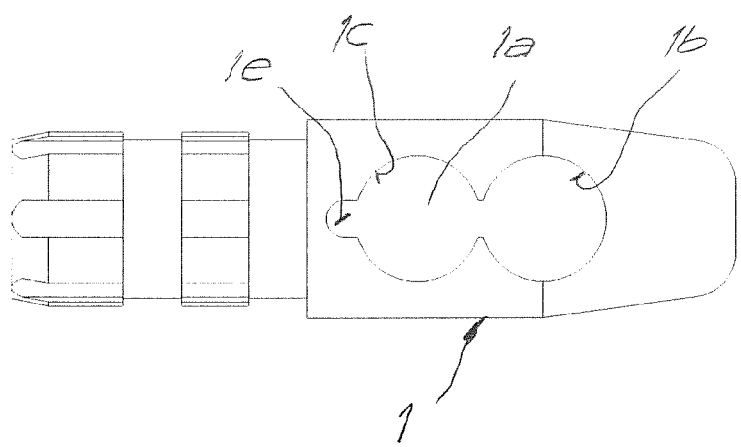
FIG. 4 is a side view of the working head of a catheter according to FIGS. 1 to 3.
Figure 5:
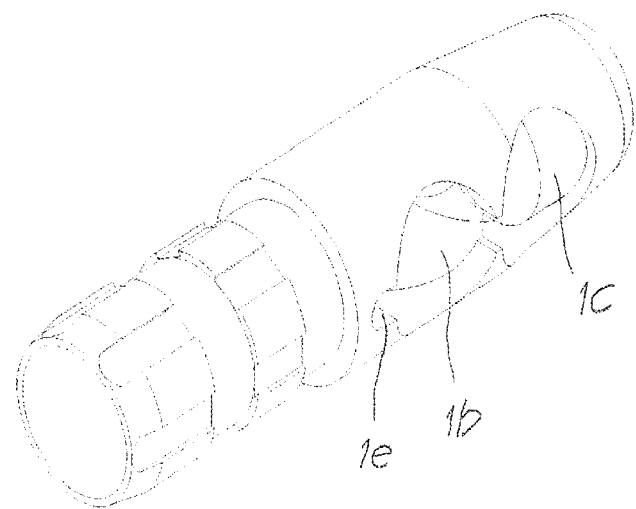
FIG. 5 is a perspective view of the working head according to FIG. 4.

The catheter according to the invention, which can be seen from FIGS. 1 to 3, basically consists of a working head 1, a tube 2 connected rigidly thereto and a feed screw 3 which can be rotated by a drive unit (not shown) which is known per se and is arranged at the proximal end of the catheter. A guide wire 4 passes through the catheter axially along its entire length. When the catheter is used it is displaced along the guide wire 4, which is first inserted into the blood vessel to be treated, as far as the treatment site. This procedure is carried out by the doctor, generally under X-ray control.

The working head is preferably tapered toward its distal end. This facilitates the insertion of the catheter into the partly narrowed blood vessels and prevents any internal injuries during the process.

The feed screw 3 is axially biased and is supported on the working head 1 by a thrust bearing 5. With rotation of the feed screw 3 at high speed (for example approximately 50,000 rpm) in the direction of rotation R, this biasing reduces the vibrations on the feed screw 3. In addition, this biasing provides clearly defined conditions of engagement with cooperation between the feed screw 3 and the working head 1. When the removed and size-reduced material is conveyed toward the proximal end of the catheter, additional stresses F are produced which have to be taken up by the thrust bearing 5.

Figure 6:
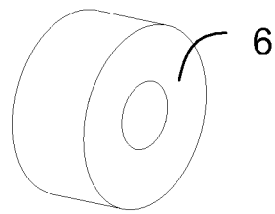
FIG. 6 is a perspective view of the thrust bearing.

As can be seen clearly from the longitudinal section in FIG. 3 and in FIG. 6, the thrust bearing 5 consists substantially of a perforated disc 6 which is arranged between the distal end of the feed screw 3 and a shoulder 1d of the working head 1. The disc 6 consists of a hard, abrasion-resistant plastics material with good sliding properties. The lubrication and friction conditions between the disc 6 and the feed screw 3 on the one hand, and between the disc 6 and the working head 1 on the other are approximately identical. The relative rotation, which is caused by entrainment, between the disc 6 and the rotating feed screw 3 is thus approximately identical to that between the disc 6 and the stationary working head 1. This means that the disc 6 is caused to co-rotate at approximately half the speed of rotation of the feed screw 3 when the catheter is driven. Wear is thus reduced and the development of heat as a result of friction in the catheter is also reduced.

As can be seen from FIGS. 1, 2, 4 and 5, the working head 1 comprises lateral openings 1a. These openings 1a are formed, for example, as circular holes 1b, 1c arranged axially in succession. The axial distance between the two holes 1b, 1c is preferably selected in such a way that the circumferences of the holes 1b, 1c overlap, i.e. the axial spacing between the holes 1b, 1c is slightly smaller than the diameter of the holes 1b, 1c. A slit 1e which extends in the axial direction is arranged at the proximal end of the openings 1a and the holes 1b, 1c. Both the inner edges of the holes 1b, 1c and those of the slit 1e are preferably sharp-edged, and in each case a total of five cutting edges 1f, 1g, 1h, 1l and 1k are formed per opening 1a, as can be seen from FIG. 2.

By contrast, in order to achieve favourable flow conditions in the region of the lateral openings 1a, the edges of the lateral openings 1a are formed, at least over regions, as chamfers ('roundings') 1l in the region of the outer surface of the working head 1.

Figure 7:
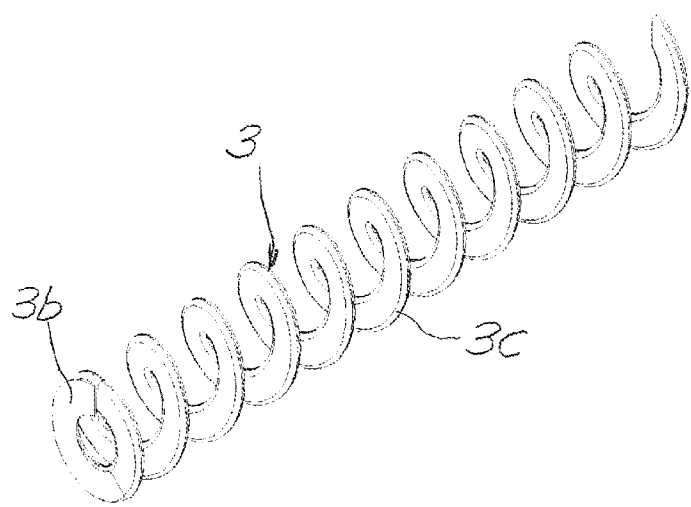
FIG. 7 is a perspective view of the drive and feed screw.

The feed screw 3 illustrated in FIG. 7 comprises planar end turns 3b. At the distal end of the feed screw 3 this end turn 3b lies on the disc 6 forming the thrust bearing 5. The edges 3c on the outer face of the feed screw 3 are sharp-edged, at least in the region of the working head 1. These edges 3c, together with the cutting edges 1f, 1g, 1h, 1i and 1k of the working head 1, cut and size-reduce the material to be removed which has been aspirated into the catheter.

LIST OF REFERENCE NUMERALS 1 working head
1a opening
1b hole
1c hole
1d shoulder
1e slit
1f cutting edge
1g cutting edge
1h cutting edge
1l cutting edge
1k cutting edge
1l chamfer ('rounding')
2 tube
3 feed screw
3a distal end
3b end turn
3c edge
4 guide wire
5 (axial) thrust bearing
6 disc
F stress
R direction of rotation

The invention claimed is:

1. A catheter for aspirating, fragmenting and removing extractable material from hollow bodies, in particular thrombi and emboli from blood vessels, comprising:
   a working head, which has an inner diameter of an inner surface, arranged at a distal end of the catheter and axially displaceable along a guide wire, independently thereof, which working head comprises at least one lateral opening;
   a flexible tube connected to the working head to remove the material or the detached thrombi and emboli fragments; and
   a flexible feed screw disposed within the flexible tube and the working head, the flexible feed screw having an outer diameter, a distal end and a proximal end, and rotating at a speed of rotation by means of a rotary drive of a drive unit remote from the working head, the feed screw being designed as a shearing cutting tool which cooperates with the opening in the working head in order to size-reduce the materials or aspirated and/or detached thrombi and emboli which penetrate between the peripheral edges of the feed screw and edges of the at least one lateral opening; and
   a thrust bearing arranged between the distal end of the feed screw and the working head, the thrust bearing being designed as a disc which is rotated by the feed screw during operation.

2. The catheter according to claim 1, wherein the disc includes a material with a low coefficient of friction, preferably of plastics material.

3. The catheter according to claim 1, wherein the feed screw is biased under axial pressure by the thrust bearing.

4. The catheter according to claim 3, wherein the biasing pressure of the feed screw is adjustable, the biasing pressure of the feed screw preferably being set in such a way that the thrust bearing co-rotates at approximately half the speed of rotation of the feed screw.

5. The catheter according to claim 1, wherein the at least one lateral opening in the working head is formed as circular holes, each having a circumference.

6. The catheter according to claim 5, wherein the at least one lateral opening in the working head is formed in each case as at least two holes arranged axially in succession.

7. The catheter according to claim 6, wherein the circumferences of the holes overlap.

8. The catheter according to claim 6, wherein the holes are interconnected by a slit which extends in the axial direction and is arranged substantially centrally to the holes.

9. The catheter according to claim 8, wherein the slit extends beyond the holes toward the proximal end of the catheter.

10. The catheter according to claim 1, wherein two approximately diametrically opposed openings are arranged in the working head.

11. The catheter according to claim 1, wherein the outer diameter of the distal part of the feed screw in the region of the working head is designed so as to fit precisely against the inner diameter of the preferably cylindrical working head, in such a way that the outer diameter of the feed screw has only minimal diametrical play relative to the inner diameter of the inner surface of the working head.

12. The catheter according to claim 1, wherein edges are provided on the outer face of the feed screw and are sharp-edged, at least in the region of the opening in the working head.

13. The catheter according to claim 1, wherein the working head is tapered toward its distal end.

14. The catheter according to claim 1, wherein the lateral opening comprises cutting edges in the region of the inner surface of the working head, which cutting edges are sharp-edged, at least over portions.

15. The catheter according to claim 1, wherein edges of the lateral opening are rounded, at least over portions, in the region of the outer surface of the working head.

\* \* \* \* \*